United States Patent [19]

Albright et al.

[11] 4,350,822

[45] Sep. 21, 1982

[54] ANTILIPIDEMICPARA-[ARYL(ALKYL OR ALKENYL)AMINO]BENZOIC ACID DERIVATIVES

[75] Inventors: Jay D. Albright, Nanuet; Thomas G. Miner, Chester; Robert G. Shepherd, South Nyack, all of N.Y.

[73] Assignee: American Cyanamid Company, Stamford, Conn.

[21] Appl. No.: 20,766

[22] Filed: Mar. 15, 1979

Related U.S. Application Data

[62] Division of Ser. No. 557,550, Mar. 12, 1975, Pat. No. 4,185,115.

[51] Int. Cl.$^3$ .................. C07C 101/60; C07C 101/62; A61K 31/195; A61K 31/245
[52] U.S. Cl. ........................................ 560/45; 560/47; 560/48; 562/452; 562/456; 562/457; 424/310; 424/319
[58] Field of Search .............................. 560/47, 45, 48; 562/457, 456, 452

[56] References Cited

U.S. PATENT DOCUMENTS

| | | | |
|---|---|---|---|
| 2,821,485 | 1/1958 | Provine et al. | 562/457 |
| 3,868,416 | 2/1975 | Albright et al. | 260/501.11 |
| 3,957,850 | 5/1976 | Bouchara | 562/457 |
| 4,058,550 | 11/1977 | Shepherd et al. | 560/43 |
| 4,105,791 | 8/1978 | Wagner et al. | 560/43 |
| 4,143,151 | 3/1979 | Wagner et al. | 424/310 |

FOREIGN PATENT DOCUMENTS

| | | |
|---|---|---|
| 350532 | 11/1978 | Austria . |
| 2340726 | 9/1977 | France . |
| 2361340 | 3/1978 | France . |

OTHER PUBLICATIONS

Skita et al., Chem. Absts., 38, 2346, 1944.
Birnbaum et al., Chem. Absts. 40, 559, 1946.
Aumüller et al., Chem. Absts., 48, 649, 1954.
Mondon, Chem. Absts., 54, 13154, 1960.
Hayes et al., J. Chem. Soc., 1088 (1970).
Derwent Abstract, Reporting on 7/19/77 Belgium Pat. 850,517.
Derwent Abstract, Reporting on 8/8/77 Belgium Pat. 851,184.
Nakanishi et al., Chem. Absts., 82, 170414(y), 1975.
Provine et al., Chem. Absts., 52, 8539(d), 195.

*Primary Examiner*—Joseph E. Evans
*Attorney, Agent, or Firm*—Jack W. Richards

[57] ABSTRACT

Novel para-[aryl(alkyl or alkenyl)amino]benzoic acids, esters, pharmaceutically acceptable salts and pharmaceutical compositions thereof and a method of lowering serum lipid levels in mammals therewith.

17 Claims, No Drawings

ANTILIPIDEMIC PARA-[ARYL(ALKYL OR ALKENYL)AMINO]BENZOIC ACID DERIVATIVES

CROSS REFERENCE TO RELATED APPLICATION

This application is a division of our copending application Ser. No. 557,550, filed Mar. 12, 1975, now U.S. Pat. No. 4,185,115.

BACKGROUND OF THE INVENTION

Considerable effort has been directed in recent years toward obtaining substances which are useful in the treatment of hyperlipidemia, a condition associated with elevated serum lipid levels, e.g., elevated cholesterol, phospholipid and/or triglyceride serum levels. This condition is associated with a number of diseases, one of the most serious being atherosclerosis. Medicaments used to lower cholesterol, phospholipid and triglyceride serum levels are termed hypolipidemic or antilipidemic drugs. Presently three major lipid-lowering agents are available: clofibrate, D-thyroxine, and nicotinic acid. [R. I. Levy and D. S. Fredrickson, Postgraduate Medicine, Vol. 47, pps. 130–136 (1970).] The class of lipid lowering compounds encompassed by the present invention may be referred to as para-[aryl(alkyl or alkenyl)amino]benzoic acid derivatives.

U.S. Pat. No. 3,716,664 discloses and claims a method of lowering serum lipid levels in mammals by the administration of certain meta and para alkoxybenzoic acids, esters, pharmaceutically acceptable salts and pharmaceutical compositions thereof. U.S. Pat. No. 3,868,416 discloses and claims certain 4-(monoalkylamino)benzoic acids, esters, pharmaceutically acceptable salts, pharmaceutical compositions thereof and a method of lowering serum lipid levels in mammals therewith. German Pat. No. 716,668 discloses the compound p-[(3-phenylpropyl)amino]benzoic acid, however, no utility other than that in a chemical process is given for the compound. The compound p-benzylaminobenzoic acid is disclosed in Chemical Abstracts 42:5033b, 43:2487e, 48:649b, 48:32846c and 49:10886g; ethyl p-benzylaminobenzoate in Chemical Abstracts 38:P2346[2], 51:8720g and J. Org. Chem. 26:1437 (1961); p-[(p-methoxybenzyl)amino]benzoic acid in J. Chem. Soc. 1088 (1970); ethyl p-($\beta$-phenethylamino)benzoate and p-($\beta$-phenethylamino)benzoic acid in Chemical Abstracts 40:559[3]; and the compound p-[$\beta$-(3,4-dimethoxyphenyl)ethylamino]benzoic acid in Chemical Abstracts 54:13154g. No prior art is known which discloses the para-[aryl(alkyl or alkenyl)amino]benzoic acid derivatives of this invention and/or their utility as antilipidemic agents.

SUMMARY OF THE INVENTION

This invention is concerned with and contemplates as novel antilipidemic compounds those compounds which may be referred to as para-[aryl(alkyl or alkenyl)amino]benzoic acid derivatives and which may be represented by the formula:

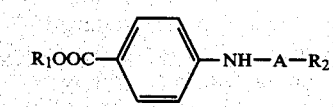

wherein $R_1$ is selected from the group hydrogen, lower alkyl, benzyl, diloweralkylaminoethyl and loweralkoxyethyl; $R_2$ is selected from the group aryl and substituted aryl; A is selected from the group $C_nH_{2n}$, wherein $n=1-16$ (with the proviso that when $n=1$ or 2, $R_2$ must not be phenyl, monomethoxy- or dimethoxyphenyl and when $n=3$ and $R_1=H$, $R_2$ must be substituted aryl) and $C_nH_{2n-2}$, wherein $n=3-16$; the pharmaceutically acceptable acid addition salts thereof; and when $R_1=H$, the alkali metal or organic base carboxylic acid salts thereof.

Suitable lower alkyl groups contemplated by this invention are those having 1–6 carbon atoms, as, for example, methyl, ethyl, isopropyl, propyl, tert-amyl and n-hexyl. Suitable lower alkenyl groups contemplated are allyl, 1, 2 or 3-butenyl, and pentenyl. Suitable $C_nH_{2n}$ and $C_nH_{2n-2}$ groups are both branched and straight chain. Suitable aryl and substituted aryl groups include, for example, phenyl, substituted phenyl such as 4-halophenyl, 2,4-dihalophenyl, 2,4,6-trihalophenyl, 4-lower alkoxyphenyl, 2,4-di-loweralkoxyphenyl, 2,4,6-tri-loweralkoxyphenyl, 4-benzyloxyphenyl, 4-loweralkylphenyl, 2,4-di-loweralkylphenyl, 2,4,6-tri-loweralkylphenol, 1-naphthyl, 2-naphthyl, 2-furoyl, 2-thienyl and biphenyl.

As a method of lowering serum lipid levels in mammals, this invention contemplates and comprises orally administering to said mammals an effective lipid-lowering amount of a para-[aryl(alkyl or alkenyl)amino]benzoic acid derivative of the formula:

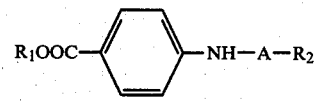

wherein $R_1$ is selected from the group hydrogen, lower alkyl, benzyl, diloweralkylaminoethyl and loweralkoxyethyl; $R_2$ is selected from the group aryl and substituted aryl; A is selected from the group $C_nH_{2n}$, wherein $n=1-16$ and $C_nH_{2n-2}$, wherein $n=3-16$; the pharmaceutically acceptable salts thereof; and when $R_1=H$, the alkali metal or organic base carboxylic acid salts thereof.

This invention also contemplates a therapeutic composition in unit dosage form which is useful to lower serum lipid levels in mammals comprising a para-[aryl(alkyl or alkenyl)amino]benzoic acid derivative of the formula:

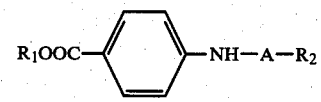

wherein $R_1$ is selected from the group hydrogen, lower alkyl, benzyl, diloweralkylaminoethyl and loweralkoxyethyl; $R_2$ is selected from the group aryl and substituted aryl; A is selected from the group $C_nH_{2n}$, wherein $n=1-16$ and $C_nH_{2n-2}$, wherein $n=3-16$; the pharmaceutically acceptable salts thereof; and when $R_1=H$, the alkali metal or organic base carboxylic acid salts thereof, in concentration per dosage unit to provide a daily dosage of from about 35 mg. to about 2.8 g., preferably from about 140 mg. to about 2.0 g.; and a pharmaceutical carrier.

DETAILED DESCRIPTION OF THE INVENTION

The novel para-[aryl(alkyl or alkenyl)amino]benzoic acid derivatives of the present invention are in general colorless or tan crystalline solids with some being colorless or tan oils. The compounds are soluble in organic solvents such as benzene, chloroform, dichloromethane, N,N-dimethylformamide, dimethylsulfoxide and lower alkanols. They are bases and may be converted to their non-toxic addition salts with acids such as sulfuric, hydrochloric, phosphoric, succinic, citric and the like. The compounds wherein $R_1$ is hydrogen may be reacted with alkali bases such as sodium hydroxide and potassium hydroxide or with organic bases such as ammonium hydroxide, pyridine, mono-, di-, or tri-lower alkylamines such as methylamine, diethylamine, trimethylamine, dibutylamine and the like to obtain the corresponding carboxylic acid salts.

The novel para-[aryl(alkyl or alkenyl)amino]benzoic acid derivatives of this invention are prepared by reacting lower alkyl p-aminobenzoates with alkylating agents such as arylalkyl or arylalkenyl halides, arylalkanol or arylalkenol O-sulfates, O-tosylates, O-trifluoromethylsulfonates, O-methanesulfonates with or without solvent at 50° C. to 150° C. Suitable solvents are hexamethylphosphoramide, N,N-dimethylformamide, N,N-dimethylacetamide, lower alkanols, chloroform, dimethylsulfoxide, benzene, xylene, acetonitrile and the like. The reaction may be carried out with an equivalent of base such as an alkali carbonate or bicarbonate.

Alternatively, the arylalkyl or arylalkenyl aminobenzoates may be prepared by reaction of a lower alkyl p-aminobenzoate with an arylalkyl or arylalkenyl halide, in the presence of an equivalent of sodium hydride in an inert solvent such as hexamethylphosphoramide, N,N-dimethylformamide, N,N-dimethylacetamide and xylene at 50° C. to 150° C. In the case or arylalkyl or arylalkenyl chlorides the alkylation of lower alkyl p-aminobenzoates may be carried out in an inert solvent such as hexamethylphosphoramide, N,N-dimethylformamide and N,N-dimethylacetamide with an equivalent of dry sodium iodide or potassium iodide to promote the reaction.

The p-arylalkyl and p-arylalkenyl aminobenzoic acids are prepared by hydrolysis of the corresponding benzoate esters by reacting with an alkali metal hydroxide such as sodium or potassium hydroxide in a lower alkanol, water or an aqueous lower alkanol at 25° C. to 100° C. Alternatively, the acids may be prepared by hydrolysis of the lower alkyl benzoates with mineral acids such as hydrochloric, hydrobromic, sulfuric, in water or aqueous lower alkanols.

Esters of p-arylalkyl- and p-arylalkenyl aminobenzoic acids may be prepared by conversion of the appropriate acid to an acid chloride with reagents such as thionyl chloride and oxalyl chloride and then reacting the intermediate acid chloride with lower alkanols, dilower alkylaminoethanol, lower alkoxyethanol and the like.

Alternatively, the novel arylalkylaminobenzoates may be prepared by reductive alkylation of a lower alkyl p-aminobenzoate or p-aminobenzoic acid with a suitable arylalkyl-aldehyde or ketone in the presence of noble metals and (or) nickel or cobalt catalysts or a suitable metal hydride. For example, Raney nickel hydrogen and an arylalkylaldehyde may be used to reductively alkylate ethyl p-aminobenzoate. Auxiliary catalysts such as aluminum chloride, piperidine acetate or acids may be used in the reductive alkylation. Similarly, arylalkenylaminobenzoates may be prepared by reductive alkylation of a suitable arylalkenylaldehyde or ketone in the presence of noble metals and (or) nickel or cobalt catalyst or a suitable metal hydride.

EXAMPLE 1

Preparation of p-(Phenethylamino)benzoic acid

A mixture of 16.5 g. of ethyl p-aminobenzoate, 10.3 g. of (2-bromoethyl)benzene and 50 ml. of hexamethylphosphoramide is heated in an oil bath at 115°–120° C. for 17 hours. The mixture is put into ice and water and extracted with ether. The ether extracts are washed with water, dried over magnesium sulfate and concentrated in vacuo to an oil. The oil is combined with 200 ml. of ethanol-water (9:1) and 20 g. of potassium hydroxide and the mixture is refluxed for 3.5 hours. After chilling the mixture is made acidic with concentrated hydrochloric acid, diluted with 150 ml. of water, chilled, diluted with water and extracted with chloroform. The chloroform extracts are washed with water, dried over magnesium sulfate and concentrated in vacuo to a gum. Ethanol is added, the mixture is chilled and filtered to give yellow crystals. The mother liquors are chilled at −20° C. to give a second crop of crystals. Recrystallization of the combined crops of crystals from hexane-ethanol gives yellow crystals, m.p. 123°–125° C. Recrystallization from ethanol gives pale yellow crystals, m.p. 124°–126° C.

EXAMPLE 2

Preparation of p-(Decyloxy)benzyl alcohol

To 100 ml. of 1.0 M borane in tetrahydrofuran cooled in an ice bath under nitrogen is added dropwise, 27.8 g. of p-decyloxybenzoic acid in 300 ml. of tetrahydrofuran over a period of 45 minutes. The mixture is stirred at room temperature for 6 hours and poured onto ice, diluted with water and 10 ml. of concentrated hydrochloric acid. The mixture is filtered and the solid washed with water to give white crystals. Recrystallization from ethanol gives white plates, m.p. 57.5°–59° C.

EXAMPLE 3

Preparation of p-(Decyloxy)benzyl alcohol o-methanesulfonate

A mixture of 15.9 g. of p-(decyloxy)benzyl alcohol (prepared as described in Example 2) and 9.1 ml. of triethylamine in 300 ml. of dichloromethane is chilled to −15° C. in an ice-salt bath. To the solution is added dropwise 5.1 ml. of methanesulfonyl chloride in 5 ml. of dichloromethane over a period of 10 minutes. The mixture is stirred at −15° C. for 30 minutes and at −8° C. for 10 minutes. The mixture is washed with 100 ml. of ice cold water, 100 ml. of cold 10% hydrochloric acid, 100 ml. of cold saturated sodium bicarbonate and with 100 ml. of cold saturated sodium chloride solution. The organic layer is dried over magnesium sulfate and the solvent removed in vacuo. The residue is dissolved in dichloromethane and extracted with saturated sodium bicarbonate solution. The organic layer is dried over magnesium sulfate and concentrated in vacuo to give a pale yellow oil.

EXAMPLE 4

Preparation of p-{[p-(Decyloxy)benzyl]amino}benzoic acid

A mixture of 16.5 g. of ethyl p-aminobenzoate, 15.6 g. of p-(decyloxy)benzyl alcohol O-methanesulfonate (prepared as described in Example 3) and 50 ml. of hexamethylphosphoramide is heated at 120° C. for 22 hours. The solution is cooled, diluted with 10 ml. of water and 50 ml. of ethanol and chilled. Filtration gives a solid which is washed with 50 ml. of ethanol and with water. A second crop is obtained from the filtrate. The two crops of gummy solid are heated with ethanol and the solvent decanted until 200 ml. of extract is obtained (some oily insoluble solid remains). The ethanol extracts are chilled, filtered and the solid washed once with ethanol to give tan crystals. Recrystallization from ethanol gives off-white crystals.

The solid is combined with 50 ml. of ethanol, 10 ml. of water and 6 g. of potassium hydroxide and the mixture refluxed for 4 hours. The mixture is diluted with 10 ml. of water, acidified with concentrated hydrochloric acid, diluted with water and chilled. Filtration gives a solid which is washed with water, dried and washed with benzene (50 ml.) to give crystals, m.p. 130°–135° C. and 158°–160° C. Recrystallization from ethanol and from acetone gives white crystals, m.p. 131°–134° C. and 159°–161° C.

EXAMPLE 5

Preparation of Ethyl p-[(4-biphenylmethyl)amino]benzoate and p-[(4-Biphenylmethyl)amino]benzoic acid A mixture of 16.5 g. of ethyl p-aminobenzoate, 10.1 g. of 4-chloromethylbiphenyl and 50 ml. of hexamethylphosphoramide are heated at 120° C. for 22 hours. The mixture is chilled, diluted with 18 ml. of water, chilled and filtered. The solid is washed with water and with ethanol to give tan crystals. Recrystallization from a mixture of 300 ml. of ethanol and 75 ml. of benzene gives tan crystals, m.p. 165°–168° C. Recrystallization from acetone gives tan crystals, m.p. 164°–167° C.

A mixture of 5 g. of the above ethyl ester, 5 g. of potassium hydroxide and 100 ml. of ethanol-water (9:1) is refluxed for 3 hours. The mixture is acidified with concentrated hydrochloric acid, diluted with 25 ml. of water, chilled and filtered to give pale yellow crystals, m.p. 231°–235° C. Recrystallization from ethanol-benzene gives yellow crystals, m.p. 234°–237° C.

EXAMPLE 6

Preparation of 11-Phenyl-1-undecanol

To 200 ml. of 1 M borane in tetrahydrofuran, cooled in an ice bath under nitrogen, is added dropwise over 35 minutes, a solution of 52.5 g. of phenylundecanoic acid in 150 ml. of tetrahydrofuran. The solution is allowed to stand at room temperature for 5.5 hours and poured onto ice. To the mixture is added 8 ml. of concentrated hydrochloric acid and the mixture is diluted with water to 2.2 liters. The mixture is extracted with ether (ca 500 ml.) and the extracts dried over magnesium sulfate. Concentration in vacuo gives a colorless oil.

EXAMPLE 7

Preparation of 11-Phenyl-1-undecanol O-methanesulfonate

To a mixture of 750 ml. of dichloromethane, 37.2 g. of 11-phenyl-1-undecanol (prepared as described in Example 6) and 32 ml. of triethylamine cooled in an ice-salt bath to −10° C. is added dropwise, over 15 minutes, 13.2 ml. of methanesulfonyl chloride. The mixture is cooled at −10° C. to −15° C. for 30 minutes and then washed with 300 ml. of cold water, 300 ml. of cold 10% hydrochloric acid, 300 ml. of cold 5% sodium carbonate and with 200 ml. of cold, saturated, sodium chloride solution. The organic layer is dried over magnesium sulfate and concentrated in vacuo to give a pale yellow oil.

EXAMPLE 8

Preparation of p-[(11-Phenylundecyl)amino]benzoic Acid

A mixture of 16.5 g. of ethyl p-aminobenzoate, 16.3 g. of 11-phenylundecanol O-methanesulfonate (prepared as described in Example 7) and 50 ml. of hexamethylphosphoramide are heated in an oil bath at 120° C. for 20 hours. The mixture is poured into ice and water and extracted with chloroform. The extracts are washed with water, 0.1 N NaOH, saturated sodium chloride solution and water. After drying over magnesium sulfate the extract is filtered through silica gel and the silica gel is washed with chloroform. The filtrate is concentrated in vacuo to an oil which is combined with 200 ml. of ethanol-water (9:1), 15 g. of potassium hydroxide and the mixture is refluxed for 3.5 hours. The mixture is acidified with concentrated hydrochloric acid, diluted with 50 ml. of water and chilled. Dilution with 100 ml. of ethanol and 25 ml. of water and filtration gives a gummy solid which is washed with water. The solid is dissolved in hexane:ether:ethyl acetate:acetic acid (40:5:5:2) and filtered through silica gel G. The support is washed with the same solvent (2 fractions). The first fraction is concentrated in vacuo to an oil which is crystallized from hexane to give pale yellow crystals, m.p. 50°–52° C. Recrystallization from ether-hexane (1:1) gives white crystals, m.p. 53°–55° C.

EXAMPLE 9

Preparation of Ethyl p-benzylaminobenzoate

A mixture of 16.5 g. of ethyl p-aminobenzoate, 8.55 g. of benzyl bromide and 45 ml. of hexamethylphosphorimide are heated in an oil bath at 110° C. for 20 hours. The mixture is diluted with water, chilled, filtered and the solid washed with water to give tan crystals, m.p. 90°–93° C. A sample is recrystallized from ethanol to give tan crystals, m.p. 96°–97° C.

EXAMPLE 10

Preparation of p-Benzylaminobenzoic Acid

A mixture of 6.0 g. of ethyl p-benzylaminobenzoate (prepared as described in Example 9), 100 ml. of ethanol-water (9:1) and 6.0 g. of potassium hydroxide are refluxed for 3.5 hours. The mixture is acidified with concentrated hydrochloric acid, diluted with water, chilled, filtered and the solid washed with water to give pale cream crystals, m.p. 165°–168° C. Recrystallization from ethanol gives tan crystals, m.p. 167°–169° C.

EXAMPLE 11

Preparation of Ethyl p-[p-(benzyloxy)benzylamino]benzoate

A mixture of 16.5 g. of ethyl p-aminobenzoate, 11.64 g. of p-benzyloxybenzyl chloride and 50 ml. of hexamethylphosphoramide are heated in an oil bath at 110° C. for 20 hours. The mixture is chilled, diluted with 25 ml. of water, chilled and the solid mass diluted with additional water in order to filter. The solid is washed with water and recrystallized from ethanol to give off-white crystals, m.p. 144°–146° C. A sample is recrystallized from ethanol to give off-white crystals, m.p. 146°–147° C.

EXAMPLE 12

Preparation of p-[p-(Benzyloxy)benzylamino]benzoic Acid

A mixture of 10 g. of ethyl p-[p-(benzyloxy)benzylamino]benzoate (prepared as described in Example 11) 10 g. of potassium hydroxide and 200 ml. of ethanol-water (9:1) are refluxed for 4.5 hours. While hot, the mixture is acidified with concentrated hydrochloric acid. Dilution with water and filtration gives tan crystals which are recrystallized from glacial acetic acid to give off-white crystals, m.p. 206°–208° C.

EXAMPLE 13

Preparation of p-[6-(Phenylhexyl)amino]benzoic Acid

A solution of 8.13 g. of ethyl p-[6-(phenylhexyl)amino]benzoate and 2.81 g. of potassium hydroxide in 90 ml. of 95% ethanol is heated at reflux for 5 hours. Five ml. of concentrated HCl is added to the hot reaction mixture. The mixture is cooled to room temperature, 100 ml. of water is added and the mixture is refrigerated. The product is collected by filtration, washed with water, dried and then recrystallized from absolute ethanol yielding tan needles, m.p. 126°–129° C.

EXAMPLE 14

Preparation of Ethyl p-[(p-Methoxybenzyl)amino]benzoate

A mixture of 33 g. of ethyl p-aminobenzoate, 100 ml. of hexamethylphosphoramide and 15.7 g. of p-(chloromethyl)anisole are heated at 100°–110° C. for 22 hours. The solution is chilled, diluted with 60 ml. of water, chilled, filtered and the solid washed with ethanol and with water to give yellow crystals. Recrystallization from ethanol gives pale yellow crystals, m.p. 128°–130° C.

EXAMPLE 15

Preparation of p-[(p-Methoxybenzyl)amino]benzoic Acid

A mixture of 15 g. of ethyl p-[(p-methoxybenzyl)amino]benzoate, (prepared as described in Example 14) 15 g. of potassium hydroxide and 200 ml. of ethanol-water (9:1) are refluxed for 3 hours, acidified while hot with concentrated hydrochloric acid, diluted with water, cooled, filtered and the solid is washed with water to give tan crystals, m.p. 208°–210° C. Recrystallization from ethanol gives off-white crystals, m.p. 209°–210° C.

EXAMPLE 16

Preparation of p-(Benzyloxy)phenethanol

To 120 ml. of 1.0 M borane in tetrahydrofuran cooled in an ice bath is added dropwise 14.5 g. of (p-benzyloxyphenyl)acetic acid in 100 ml. of dry tetrahydrofuran over a period of 25 minutes. After 17 hours at room temperature the mixture is poured onto ice. After the ice melts filtration gives white crystals, m.p. 72°–75° C.

EXAMPLE 17

Preparation of p-(Benzyloxy)phenethanol O-methanesulfonate

To a mixture of 250 ml. of dichloromethane, 11.42 g. of p-(benzyloxy)phenethanol (prepared as described in Example 16) and 10.7 ml. of triethylamine chilled to −10° C. is added dropwise over 10 minutes 6.23 g. (4.21 ml.) of methanesulfonyl chloride in 10 ml. of dichloromethane. After 45 minutes the mixture is washed with 100 ml. of ice cold water, 100 ml. of 10% hydrochloric acid, 100 ml. of cold saturated sodium bicarbonate solution, 100 ml. of saturated sodium chloride, dried over magnesium sulfate and the solvent removed in vacuo. The oil crystallizes to give white crystals, m.p. 62°–65° C.

EXAMPLE 18

Preparation of Ethyl p-[(p-Benzyloxyphenethyl)amino]benzoate

A mixture of 16.5 g. of ethyl p-aminobenzoate, 15.3 g. of p-(benzyloxy)phenethanol O-methanesulfonate (prepared as described in Example 17) and 50 ml. of hexamethylphosphoramide is heated in an oil bath at 110° C. for 20 hours. The solution is chilled, diluted with 30 ml. of water, 10 ml. of ethanol, chilled, filtered and the solid is washed with aqueous ethanol and with water. The solid is recrystallized (twice) from ethanol to give tan crystals, m.p. 94°–97° C. Recrystallization from ethanol gives tan crystals, m.p. 95°–97° C.

EXAMPLE 19

Preparation of p-[(p-Benzyloxyphenethyl)amino]benzoic Acid

A mixture of 6.0 g. of ethyl p-[(p-benzyloxyphenethyl)amino]benzoate (prepared as described in Example 18) 6.0 g. of potassium hydroxide and 100 ml. of ethanol-water (9:1) is refluxed for 3.5 hours. The mixture is acidified while hot with concentrated hydrochloric acid, diluted with water, filtered and the solid washed with water to give tan crystals, m.p. 180°–185° C. Recrystallization from glacial acetic acid gives tan crystals, m.p. 187°–189° C.

EXAMPLE 20

Preparation of p-Tridecyloxybenzyl Alcohol

To 200 ml. of 1.0 M borane in tetrahydrofuran, chilled in an ice bath is added dropwise over 30 minutes 32.0 g. of p-tridecyloxybenzoic acid in 450 ml. of tetrahydrofuran. After 22 hours at room temperature, the mixture is poured onto ice. After the ice melts, the solid is filtered and washed with water to give white crystals, m.p. 72°–75° C. Recrystallization from ethanol gives white crystals, m.p. 74°–75° C.

EXAMPLE 21

Preparation of p-(Tridecyloxy)benzyl alcohol O-methanesulfonate

To a mixture of 19.1 g. of p-(tridecyloxy)benzyl alcohol (prepared as described in Example 20), 9.1 ml. (6.51 g.) of triethylamine and 300 ml. of dichloromethane chilled to −10° C. is added dropwise over 10 minutes, 7.5 g. (5.1 ml.) of methanesulfonyl chloride in 5 ml. of dichloromethane. After stirring at −10° C. to −15° C. for one hour, the mixture is washed with 100 ml. of ice-cold water, 100 ml. of cold 10% HCl, 100 ml. of cold saturated sodium bicarbonate, 100 ml. of cold saturated sodium chloride solution and with 100 ml. of cold saturated sodium bicarbonate solution. The organic layer is dried over magnesium sulfate and concentrated to give a waxy solid.

EXAMPLE 22

Preparation of Ethyl p-[(p-tridecyloxybenzyl)amino]benzoate

A mixture of 16.5 g. of ethyl p-aminobenzoate, 19.1 g. of p-(tridecyloxy)benzyl alcohol O-methanesulfonate (prepared as described in Example 21) and 50 ml. of hexamethylphosphoramide is heated at 110° C. for 20 hours. The solution is chilled, diluted with 100 ml. of ethanol-water (1:1) chilled, filtered and the solid washed with ethanol-water (1:1), water and ethanol. The solid is recrystallized from ethanol-benzene (7:3) to give white crystals, m.p. 95°–105° C. Recrystallization from ethanol-benzene (9:1) gives white crystals, m.p. 100°–105° C.

EXAMPLE 23

Preparation of p-[(p-Tridecyloxybenzyl)amino]benzoic Acid

A mixture of 7.0 g. of ethyl p-[(p-tridecyloxybenzyl)amino]benzoate (prepared as described in Example 22), 7.0 g. of potassium hydroxide and 150 ml. of ethanol-water (9:1) is refluxed for 3.5 hours. The solution is acidified while hot, diluted with water, filtered and the solid washed with water to give white crystals, m.p. 110°–113° C. and 145°–150° C. The solid is heated with 200 ml. of glacial acetic acid and the solution chilled and filtered to give crystals, m.p. 110°–112° C. and 155°–160° C. The filtrate is diluted with water to give white crystals (pure by TLC) m.p. 108°–112° C. and 150°–155° C. The first crop of crystals is slurried in 75 ml. of acetone, filtered and the filtrate chilled and filtered. The filtrate is diluted with water to give white crystals (pure by TLC). The two crops pure by TLC are combined, dried in vacuo to give white crystals, m.p. 110°–112° C. and 155°–160° C.

EXAMPLE 24

Preparation of Ethyl p-[(Cinnamyl)amino]benzoate

A mixture of 33 g. of ethyl p-aminobenzoate 15.3 g. of (3-chloropropenyl)benzene and 80 ml. of hexamethylphosphoramide is heated in an oil bath at 110° C. for 21 hours. The solution is chilled, diluted with 25 ml. of water, chilled, filtered and the solid washed with water to give cream crystals, m.p. 123°–131° C. Recrystallization from ethanol-benzene (9:1) gives pale yellow crystals, m.p. 135°–137° C. Recrystallization from benzene gives white crystals, m.p. 135°–137° C.

EXAMPLE 25

Preparation of p-(Cinnamylamino)benzoic Acid

A mixture of 10 g. of ethyl p-(cinnamylamino)benzoate (prepared as described in Example 24), 10 g. of potassium hydroxide and 200 ml. of ethanol-water (9:1) is refluxed for 3 hours. The solution is acidified while hot with concentrated hydrochloric acid, diluted with water, cooled and filtered to give off-white crystals. Recrystallization from ethanol gives pale yellow crystals, m.p. 200°–202° C.

EXAMPLE 26

Preparation of Ethyl p-[(3-phenylpropyl)amino]benzoate

A mixture of 33 g. of ethyl p-aminobenzoate, 19.9 g. of (3-bromopropyl)benzene and 80 ml. of hexamethylphosphoramide is heated at 110° C. for 20 hours. The mixture is chilled, diluted with 25 ml. of water, chilled, diluted with 50 ml. of ethanol and filtered. The solid is washed with cold ethanol-water (1:1) to give tan crystals, m.p. 80°–83° C. Two recrystallizations from ethanol give tan crystals, m.p. 87°–89° C.

EXAMPLE 27

Preparation of p-[(3-Phenylpropyl)amino]benzoic Acid

A mixture of 10 g. of ethyl p-[(3-phenylpropyl)amino]benzoate (prepared as described in Example 26), 10 g. of KOH and 200 ml. of ethanol-water (9:1) is refluxed for 4 hours. The mixture is acidified while hot with concentrated hydrochloric acid, diluted with water, cooled and filtered to give off-white crystals. Recrystallization from ethanol gives off-white crystals, m.p. 162°–163° C.

EXAMPLE 28

Preparation of Ethyl p-[10-phenyldecyl)amino]benzoate

A mixture of 13.2 g. of ethyl p-aminobenzoate, 10.1 g. of 10-phenyldecyl chloride, 6.0 g. of sodium iodide and 50 ml. of hexamethylphosphoramide is stirred and heated in an oil bath at 110° C. for 22 hours. The mixture is chilled, diluted with 25 ml. of water, 25 ml. of ethanol, chilled and filtered. The solid is washed with water and with two 50 ml. portions of ethanol to give tan crystals, m.p. 70°–73° C. Recrystallization from ethanol gives tan crystals, m.p. 74°–76° C.

EXAMPLE 29

Preparation of p-[(10-Phenyldecyl)amino]benzoic Acid

A mixture of 7.0 g. of ethyl p-[(10-phenyldecyl)amino]benzoate (prepared as described in Example 28), 7 g. of potassium hydroxide and 100 ml. of ethanol-water (9:1) is refluxed for 3.5 hours. The mixture is acidified while hot with concentrated hydrochloric acid, diluted with water, cooled and filtered to give white crystals, m.p. 80°–87° C. Recrystallization from ethanol gives white crystals m.p. 96°–98° C.

EXAMPLE 30

Preparation of Ethyl p-[(5-phenylpentyl)amino]benzoate

A mixture of 18.2 g. of ethyl p-aminobenzoate 10.2 g. of sodium iodide, 10.0 g. of 5-phenylpentyl chloride and 60 ml. of hexamethylphosphoramide is stirred and heated at 110° C. in an oil bath for 20 hours. The mixture is chilled, diluted with 25 ml. of water and 25 ml. of ethanol, chilled and filtered. The solid is washed with 50 ml. of ethanol-water (1:1), with water and once with cold ethanol to give pale yellow crystals, m.p. 63°-64° C. Recrystallization from ethanol gives off-white crystals, m.p. 73°-75° C.

EXAMPLE 31

Preparation of p-[(5-Phenylpentyl)amino]benzoic Acid

A mixture of 7 g. of ethyl p-[(5-phenylpentyl)amino]benzoate (prepared as described in Example 46), 7 g. of potassium hydroxide and 100 ml. of ethanol-water (9:1) is refluxed for 3 hours. The mixture is acidified with concentrated hydrochloric acid while hot, diluted with water, cooled and filtered. The solid is washed with water to give white crystals, m.p. 141°-143° C. Recrystallization from ethanol gives white crystals, m.p. 142°-144° C.

EXAMPLE 32

Preparation of Ethyl p-[(8-Phenyloctyl)amino]benzoate

A mixture of 14.9 g. of ethyl p-aminobenzoate, 50 ml. of hexamethylphosphoramide, 10.1 g. of 8-phenyloctyl chloride and 6.75 g. of sodium iodide is stirred and heated in an oil bath at 110° C. for 24 hours. The mixture is chilled, diluted with 50 ml. of water and 25 ml. of ethanol, chilled and filtered. The solid is washed with ethanol-water (1:1) and with water to give crystals, m.p. 61°-68° C. Recrystallization from ethanol gives white crystals, m.p. 75°-76° C.

EXAMPLE 33

Preparation of p-[(8-Phenyloctyl)amino]benzoic Acid

A mixture of 7 g. of ethyl p-[(8-phenyloctyl)amino]benzoate (prepared as described in Example 32), 7 g. of potassium hydroxide and 100 ml. of ethanol-water (9:1) is refluxed for 3.5 hours. The mixture is acidified while hot with concentrated hydrochloric acid, diluted with water, chilled and filtered. The solid is washed with water to give off-white crystals, m.p. 113°-115° C. Recrystallization from ethanol gives white crystals, m.p. 113°-115° C.

EXAMPLE 34

Preparation of Ethyl p-[(7-Phenylheptyl)amino]benzoate

A mixture of 8.25 g. of ethyl p-aminobenzoate, 5.06 g. of 7-phenylheptylchloride, 3.6 g. of sodium iodide and 25 ml. of hexamethylphosphoramide is heated in an oil bath at 110° C. for 20 hours. The mixture is chilled, diluted with 30 ml. of ethanol-water (1:1) and with water to give crystals, m.p. 65°-67° C. Recrystallization from ethanol gives white crystals, m.p. 66.5°-68° C.

EXAMPLE 35

Preparation of p-[(7-Phenylheptyl)amino]benzoic Acid

A mixture of 5 g. of ethyl p-[(7-phenylheptyl)amino]benzoate (prepared as described in Example 34), 5 g. of KOH and 50 ml. of ethanol-water (9:1) is refluxed for 3.5 hours. The mixture is acidified while hot with concentrated hydrochloric acid, diluted with H₂O, chilled and filtered. The solid is washed with H₂O to give off-white crystals, m.p. 123°-126° C. Recrystallization from ethanol gives tan crystals, m.p. 123.5°-125° C.

EXAMPLE 36

Preparation of p-[(9-Phenylnonyl)amino]benzoic Acid

A mixture of 13.9 g. of ethyl p-aminobenzoate, 10 g. of 9-phenylnonyl chloride, 6.3 g. of sodium iodide and 50 ml. of hexamethylphosphoramide is heated at 110° C. for 20 hours. The mixture is chilled, diluted with 25 ml. of ethanol-water (1:1) and with water to give off-white crystals, m.p. 62°-65° C.

The solid is combined with 1.7 g. of potassium hydroxide, 25 ml. of ethanol-water (9:1) and the mixture refluxed for 3.5 hours. The mixture is acidified while hot with concentrated hydrochloric acid, diluted with water, filtered and the solid washed with water to give off-white crystals, m.p. 105°-107° C.

EXAMPLE 37

Preparation of 4-(2-Thienyl)butanol

To 240 ml. of 1 M borane in tetrahydrofuran chilled in an ice bath, is added dropwise, 20.4 g. of 4-(2-thienyl)butyric acid in 50 ml. of tetrahydrofuran. After the addition, the mixture is allowed to stand at room temperature for 17 hours and is poured onto ice. After standing, the mixture is extracted with ether, the ether extract washed with water, dried over magnesium sulfate and concentrated in vacuo to give a pale yellow oil.

EXAMPLE 38

Preparation of Ethyl p-[4-(2-Thienylbutyl)amino]benzoate

To a solution of 15.6 g. of 4-(2-thienyl)butanol and 20.9 ml. (15.2 g.) of triethylamine in 500 ml. of dichloromethane, cooled to −8° C. is added 8.45 ml. (12.5 g.) of methanesulfonyl chloride dropwise over 10 minutes. The mixture is stirred at −8° C. for 25 minutes, washed with 400 ml. of ice water, 200 ml. of cold 10% HCl, 200 ml. of cold saturated sodium bicarbonate and 200 ml. of cold saturated sodium chloride solution. The organic layer is dried over magnesium sulfate and concentrated in vacuo to an oil. This oil is combined with 33 g. of ethyl p-aminobenzoate and 80 ml. of hexamethylphosphoramide and the mixture heated in an oil bath at 105°-110° C. for 19 hours. The solution is chilled, diluted with 35 ml. of water, chilled, 20 ml. of ethanol is added and the mixture is filtered. The solid is washed with ethanol-water (1:1) and with water and the damp solid recrystallized from 150 ml. of ethanol to give tan crystals, m.p. 63°-65° C. Recrystallization from ethanol gives tan crystals, m.p. 65°-67° C.

EXAMPLE 39

Preparation of p-[4-(2-Thienylbutyl)amino]benzoic Acid

A mixture of 7.5 g. of ethyl p-[4-(2-thienylbutyl)amino]benzoate (prepared as described in Example 38), 7.5 g. of potassium hydroxide and 150 ml. of ethanol-water (9:1) is refluxed for 4 hours. The mixture is acidified while hot with concentrated hydrochloric acid, diluted with water, cooled and filtered. The solid is washed with water to give tan crystals, m.p. 137°-140° C. Recrystallization from ethanol gives tan crystals, m.p. 139°-141° C.

EXAMPLE 40

Preparation of p-[(p-Fluorophenethyl)amino]benzoic Acid

A mixture of 15.8 g. of 1-(2-chloroethyl)-4-fluorobenzene, 33 g. of ethyl p-aminobenzoate, 16.6 g. of potassium iodide and 100 ml. of hexamethylphosphoramide is heated at 95° C. for 15 hours. The mixture is poured into water and extracted with ether. The ether extracts are washed with water, dried over magnesium sulfate and concentrated in vacuo to an oil. To the oil is added 200 ml. of ethanol-water (9:1) and 21 g. of potassium hydroxide and the mixture is refluxed for 3.5 hours. The mixture is acidified with concentrated hydrochloric acid, diluted with water, cooled and filtered to give gray crystals. Recrystallization from ethanol gives light gray crystals, m.p. 161°–163° C.

EXAMPLE 41

Preparation of Ethyl p-[3-(o-methoxyphenyl)propyl]aminobenzoate

A mixture of 14.5 g. of ethyl p-aminobenzoate, 10 g. of 1-bromo-3-(o-methoxyphenyl)propane and 50 ml. of hexamethylphosphoramide is heated at 130° C. for 15 hours, cooled and diluted with 20 ml. of water. The mixture is chilled, diluted with 50 ml. of cold ethanol:-H₂O (1:1) and filtered. The solid is washed with three 50 ml. portions of cold ethanol-water (1:1) and with water to give crystals, m.p. 106°–109° C. Recrystallization from ethanol (100 ml.) gives yellow crystals, m.p. 111°–113° C.

EXAMPLE 42

Preparation of p-[3-(o-Methoxyphenyl)propyl]aminobenzoic Acid

A mixture of 7.0 g. of ethyl p-[3-(o-methoxyphenyl)-propyl]aminobenzoate (prepared as described in Example 41), 7.0 g. of potassium hydroxide and 100 ml. of ethanol-water (9:1) is refluxed for 3.5 hours, acidified while hot with concentrated hydrochloric acid, diluted with water and chilled. The mixture is filtered and the solid washed with water to give off-white crystals, m.p. 155°–157° C. Recrystallization from ethanol gives off-white crystals, m.p. 156°–158° C.

EXAMPLE 43

Preparation of 3-[p-(Benzyloxy)phenyl]propanol O-Methanesulfonate

To a solution of 11.0 g. of 3-[p-(benzyloxy)phenyl]-propanol and 10.4 ml. of triethylamine in 175 ml. of dichloromethane chilled to −10° C. is added dropwise, over 10 minutes, a solution of 3.89 ml. of methanesulfonyl chloride in 10 ml. of dichloromethane. The solution is stirred at −10° C. for 30 minutes, washed with 150 ml. of cold water, 75 ml. of cold 10% HCl, 75 ml. of cold saturated sodium bicarbonate, 75 ml. of cold saturated sodium chloride solution and dried over magnesium sulfate. The solvent is removed in vacuo to give off-white crystals, m.p. 65°–69° C.

EXAMPLE 44

Preparation of Ethyl p-{{3-[p-(Benzyloxy)phenyl]propyl}amino}benzoate

A mixture of 12.8 g. of 3-[p-(benzyloxy)phenyl]-propanol O-methanesulfonate (prepared as described in Example 43), 50 ml. of hexamethylphosphoramide and 16.5 g. of ethyl p-aminobenzoate is heated at 100°–105° C. for 17.5 hours. The mixture is chilled, diluted with 15 ml. of water, 30 ml. of ethanol and chilled. In order to filter, 100 ml. of ethanol-water (1:1) is added and the solid filtered and washed with ethanol-water (1:1) and with water to give tan crystals, m.p. 98°–107° C. Recrystallization from ethanol gives light tan crystals, m.p. 114°–116° C.

EXAMPLE 45

Preparation of p-{{3-[p-(Benzyloxyphenyl]propyl}amino}benzoic Acid

A mixture of 8.0 g. of ethyl p-{{3-[p-(benzyloxy)-phenyl]propyl}amino}benzoate (prepared as described in Example 44), 8 g. of KOH and 100 ml. of ethanol-water (9:1) is refluxed for 3.5 hours. The mixture is acidified while hot with concentrated hydrochloric acid, diluted with water, cooled, filtered and the solid washed with water to give tan crystals, m.p. 170°–172° C. Recrystallization from ethanol gives off-white crystals, m.p. 171°–172° C.

EXAMPLE 46

Preparation of 6-Phenylhexanol

To 100 ml. of 1 molar borane in tetrahydrofuran cooled in an ice bath is added 19.2 g. of 6-phenylhexanoic acid over a period of 30 minutes. The solution is stirred for 1.5 hours and an additional 100 ml. of 1 molar borane in tetrahydrofuran is added. After stirring overnight at room temperature the reaction mixture is poured into 500 g. of ice. The mixture is extracted with ether, the extracts washed with water, dried over magnesium sulfate and concentrated under reduced pressure to give 6-phenylhexanol as a light yellow liquid.

EXAMPLE 47

Preparation of 6-Phenylhexanol O-Methanesulfonate

To a chilled (−4° C.) solution of 19.4 g. of 6-phenyl-hexanol (prepared as described in Example 46) and 15.1 g. of triethylamine in 500 ml. of dichloromethane is added dropwise, over 5 minutes, 12.6 g. of methanesulfonyl chloride. The mixture is stirred at −10° C. for 30 minutes and the solution washed successively with 200 ml. of cold water, 200 ml. of cold 10% hydrochloric acid, 200 ml. of cold saturated sodium bicarbonate and 200 ml. of cold saturated sodium chloride solution. The organic layer is dried over magnesium sulfate and the solvent removed under reduced pressure to give 6-phenylhexanol O-methanesulfonate as an oil.

EXAMPLE 48

Preparation of Ethyl 4-[6-(phenylhexyl)amino]benzoate

A solution of 34.9 g. of ethyl p-aminobenzoate, 26.9 g. of 6-phenylhexanol O-methanesulfonate (prepared as described in Example 47) and 200 ml. of hexamethylphosphoramide is heated at 110° C. in an oil bath for 20 hours. The mixture is cooled, diluted with 100 ml. of water and filtered. The solid is washed with 60 ml. of ethanol-water (1:1) to give crude ethyl 4-(6-phenylhexylamino)benzoate. Purification gives the product as crystals, m.p. 69.5°–72.5° C.

EXAMPLE 49

Preparation of 2-(2-Thienyl)ethanol O-Methanesulfonate

A mixture of 12.8 g. of 2-(2-thienyl)ethanol, 450 ml. of dichloromethane and 20.2 g. of triethylamine is chilled to −10° C. and 12.8 g. of cold methanesulfonyl chloride is added dropwise over 30 minutes. After stirring for 1 hour, the mixture is washed with 300 ml. of cold water, 300 ml. of cold 10% hydrochloric acid, 300 ml. of cold saturated sodium bicarbonate, and 300 ml. of cold saturated sodium chloride solution. The organic layer is dried over magnesium sulfate and concentrated under vacuum to give the product as an oil.

EXAMPLE 50

Preparation of Ethyl 4-[2-(2-thienyl)ethylamino]benzoate

A mixture of 33.0 g. of ethyl p-aminobenzoate, 21.8 g. of 2-(2-thienyl)ethanol O-methanesulfonate (prepared as described in Example 49) and 100 ml. of hexamethylphosphoramide is heated in an oil bath at 125° C. for 16 hours. The mixture is chilled, diluted with 15 ml. of ethanol and 150 ml. of water. The mixture is extracted with ether and the ether extracts washed with water, dried over magnesium sulfate and concentrated in vacuo to give a crude oil. A sample of this oil is chromatographed over silica gel and the fractions containing the product are combined and recrystallized from hexane to give ethyl 4-[2-(2-thienyl)ethylamino]benzoate as yellow-tan crystals, m.p. 93°–95° C.

EXAMPLE 51

Preparation of 4-[2-(2-Thienyl)ethylamino]benzoic Acid

A mixture of 29.7 g. of crude ethyl 4-[2-(2-thienyl)ethylamino]benzoate, 29 g. of potassium hydroxide and 200 ml. of 95% ethanol is refluxed for 3 hours. The solution is diluted with 100 ml. of water and adjusted to pH 6 with concentrated hydrochloric acid. The mixture is cooled, filtered and the solid washed with ethanol-water (1:1) to give a solid. The solid is heated with 200 ml. of ethanol, filtered and the filtrate concentrated. Purification gives the product, m.p. 163°–165° C.

EXAMPLE 52

Preparation of p-Heptyloxybenzyl alcohol

To a solution of 125 ml. of 1 molar borane in tetrahydrofuran chilled in an ice bath is added 19.3 g. of p-heptyloxybenzoic acid in 160 ml. of tetrahydrofuran over a period of 45 minutes. The mixture is stirred at room temperature for 5.5 hours, poured into ice and water and 30 ml. of concentrated hydrochloric acid added. The mixture is filtered and the solid washed with water to give the product as a white waxy solid.

EXAMPLE 53

Preparation of p-Heptyloxybenzyl alcohol O-Methanesulfonate

A mixture of 17.7 g. of p-heptyloxybenzyl alcohol (prepared as described in Example 52), 16.7 ml. of triethylamine and 380 ml. of dry dichloromethane is chilled at −9° C. and 6.81 ml. of methanesulfonyl chloride is added dropwise over 5 minutes. The mixture is stirred at −9° C. for 30 minutes and the solution washed successively with 250 ml. of cold water, 200 ml. of cold water, 200 ml. of cold 10% hydrochloric acid, 250 ml. of cold saturated sodium bicarbonate and 200 ml. of cold sodium chloride solution. The organic layer is dried over magnesium sulfate and the solvent removed under reduced pressure to give the product as a yellow oil.

EXAMPLE 54

Preparation of Ethyl p-{[p-(heptyloxy)benzyl]amino}benzoate

A mixture of 13.5 g. of p-(heptyloxy)benzyl alcohol O-methanesulfonate (prepared as described in Example 53), 14.9 g. of ethyl p-aminobenzoate and 50 ml. of hexamethylphosphoramide is heated at 120° C. for 24 hours. The mixture is cooled, diluted with 40 ml. of ethanol-water (1:1) and chilled. Filtration gives a crude product which is recrystallized from 95% ethanol and from ethanol to give white crystals, m.p. 111°–113° C.

EXAMPLE 55

Preparation of p-{[p-(Heptyloxy)benzyl]amino}benzoic Acid

A mixture of 5 g. of ethyl p-[p-(heptyloxy)benzyl]amino benzoate (prepared as described in Example 54), 1.51 g. of potassium hydroxide and 50 ml. of 95% ethanol is refluxed for 5 hours. Concentrated hydrochloric acid is added and the mixture diluted with 150 ml. of water. Chilling and filtering gives crystals which are recrystallized from ethanol to give white crystals, m.p. 148°–152.5° C.

EXAMPLE 56

Preparation of p-Decylbenzyl alcohol

To 69.5 ml. of 1 molar borane in tetrahydrofuran chilled in an ice bath is added dropwise over 40 minutes a solution of 17.2 g. of p-decylbenzoic acid in 150 ml. of dry tetrahydrofuran. The mixture is refluxed for 3.5 hours, chilled, 5 ml. of concentrated hydrochloric acid is added and the mixture poured onto ice. The mixture is filtered and the solid washed with water to give white crystals.

EXAMPLE 57

Preparation of p-Decylbenzyl alcohol O-Methanesulfonate

A solution of 17.0 g. of p-decylbenzyl alcohol (prepared as described in Example 56) and 14.3 ml. of triethylamine in 330 ml. of dry dichloromethane is chilled to −5° C. to −9° C. and 5.85 ml. of methanesulfonyl chloride added dropwise with stirring over 7 minutes. The mixture is stirred at −10° C. for 30 minutes and then washed successively with 250 ml. of cold water, 200 ml. of cold 10% hydrochloric acid, 200 ml. of cold saturated sodium bicarbonate and 200 ml. of cold saturated sodium chloride solution. The extract is dried over magnesium sulfate and the solvent removed under reduced pressure to give a pale yellow oil which solidifies on standing.

EXAMPLE 58

Preparation of Ethyl p-{[(p-decyl)benzyl]amino}benzoate

A mixture of 20.7 g. of p-decylbenzyl alcohol O-methanesulfonate (prepared as described in Example 57) and 20.5 g. of ethyl p-aminobenzoate in 65 ml. of hexamethylphosphoramide is heated at 115°–124° C. in an oil bath for 24 hours. The mixture is cooled and diluted with 60 ml. of ethanol-water (1:1), chilled and filtered to give cream colored crystals, m.p. 87°-90° C.

EXAMPLE 59

Preparation of p-{[(p-Decyl)benzyl]amino}benzoic Acid

A mixture of 10 g. of ethyl p-{[(p-decyl)benzyl]amino}benzoate (prepared as described in Example 58) and 2.84 g. of potassium hydroxide in 90 ml. of 95% ethanol is refluxed for 5 hours. Concentrated hydrochloric acid is added and the mixture diluted with 100 ml. of water. Filtration gives crystals which are washed with water to give a crude product. Recrystallization from ethanol gives white crystals, m.p. 135°-136° C.

EXAMPLE 60

Preparation of Ethyl 4-[2-(α-naphthyl)ethylamino]benzoate

A solution of 4.7 g. of 2-(α-naphthyl)ethyl bromide and 6.6 g. of ethyl p-aminobenzoate in 50 ml. of hexamethylphosphoramide is stirred and heated at 110° C. for 16 hours. The mixture is cooled, diluted with 50 ml. of water and filtered to give a crude product, which is recrystallized from ethanol. Recrystallization gives ethyl 4-[2-(α-naphthyl)ethylamino]benzoate as white crystals, m.p. 104°-106° C.

EXAMPLE 61

3-(p-Chlorophenyl)propanol O-Mesylate

A solution of 27.6 g. of 3-(p-chlorophenyl)propionic acid in 50 ml. of dry tetrahydrofuran is added dropwise to 180 ml. of 1 molar borane in tetrahydrofuran chilled in an ice bath. After the addition the mixture is stirred overnight at room temperature and poured into 1 liter of ice and water. The mixture is extracted with ether and the ether extract concentrated to give 27 g. of product. This product is dissolved in 600 ml. of dichloromethane and 30.3 g. of triethylamine added. To the chilled solution (−8° C.) is added dropwise 19.0 g. of methanesulfonyl chloride over 1 hour. After stirring 30 minutes the solution is washed with 400 ml. of each of the following cold solutions; 10% hydrochloric acid, saturated sodium bicarbonate and saturated sodium chloride. The organic layer is dried over magnesium sulfate and concentrated to give 35 g. of 3-(p-chlorophenyl)propanol O-mesylate.

EXAMPLE 62

Ethyl 4-[3-(p-chlorophenyl)propylamino]benzoate

A solution of 49.5 g. of ethyl 4-aminobenzoate, 34.9 g. of 3-(p-chlorophenyl)propanol O-mesylate in 100 ml. of hexamethylphosphoramide is heated at 125°-130° C. for 16 hours. The solution is diluted with 50 ml. of tetrahydrofuran and with 150 ml. of water. Chilling and filtering gives crystals which are washed with water and recrystallized from ethanol to give 28.3 g. of light yellow crystals. Recrystallizations give the product as crystals, m.p. 122°-124° C.

EXAMPLE 63

4-[3-(p-Chlorophenyl)propylamino]benzoic acid

A mixture of 16.3 g. of ethyl 4-[3-(p-chlorophenyl)propylamino]benzoate, 16.3 g. of potassium hydroxide and 200 ml. of 95% ethanol is refluxed for 3 hours. The mixture is diluted with 100 ml. of water and brought to pH 6 with concentrated hydrochloric acid. Chilling and filtering gave 15 g. of white crystals. Recrystallization from ethanol gave 8.6 g. of white crystals, m.p. 191°-192° C.

The compounds of the present invention show hypolipidemic activity in mammals, specifically warm-blooded animals. The mechanism of action of these compounds is not known and the inventors do not wish to be limited to any particular mechanism. However, the compounds of the present invention were shown to possess hypolipidemic activity as determined by animal experiments as follows: The compounds were administered orally admixed with the diet to groups of 4-6 male rats, CFE strain from Carworth Farms. A control group of 6-8 rats was maintained on the diet alone; test groups were maintained on the diet plus the indicated percentage of compound by weight. After 6 days treatment serum sterol concentrations were determined either (1) according to the saponification and extraction method of P. Trinder, Analyst 77, 321 (1952) and the colorimetric determination of Zlatkis, et al., J. Lab. Clin. Med. 44, 486 (1953) or (2) by the extraction method of H. H. Leffler, Amer. J. Clin. Path. 31, 310 (1959), the overall method appropriately modified for use with an automatic mechanical analyzer. Serum triglycerides were estimated by the automated procedure of Kessler and Lederer ["Automation in Analytical Chemistry", Skeggs, L. T., (Ed.), Mediad, Inc., New York, 1965, p. 341]. In these tests a compound is considered to have hypolipidemic activity if it depresses serum sterol levels 15% or more below that of the controls, and/or depresses triglyceride levels by 25% or more below controls. Table I shows representative compounds of the present invention and the degree to which they depress serum sterols and triglyceride levels after a one week dosing period.

TABLE I

| Compound | % Compound in Diet | Lowering of Serum Sterol | Lowering of Serum Triglyceride |
|---|---|---|---|
| p-(Phenethylamino)benzoic acid | 0.1 | 12 | 51 |
| p-{[p-(Decyloxy)benzyl]amino}benzoic acid | 0.1 | 18 | 63 |
| p-[(4-Biphenylylmethyl)amino]benzoic acid | 0.1 | 10 | 61 |
| Ethyl p-[(4-biphenylylmethyl)amino]benzoate | 0.1 | 6 | 52 |
| p-[(11-Phenylundecyl)amino]benzoic acid | 0.1 | 16 | 26 |
|  | 0.05 | 22 | 31 |
| p-Benzylaminobenzoic acid | 0.1 | 13 | 35 |
| p-[6-(Phenylhexyl)amino]benzoic acid | 0.1 | 16, 15[1] | 60, 52[1] |
|  | 0.05 | 16 | 54 |
| Ethyl p-[(p-methoxybenzyl)amino]benzoate | 0.1 | 16 | 52 |
| p-[(p-Tridecyloxybenzyl)amino]benzoic acid | 0.1 | 10 | 49 |
| p-(Cinnamylamino)benzoic acid | 0.1 | 15 | 52 |
|  | 0.05 | 29 | 51 |
| p-[(3-Phenylpropyl)amino]benzoic acid | 0.1 | 19 | 37 |
|  | 0.05 | 26 | 49 |
| trans-Ethyl-p-[(cinnamyl)amino]benzoate | 0.1 | 15 | 40 |
| Ethyl-p-[(3-phenylpropyl)amino]benzoate | 0.1 | 21 | 43 |
| Ethyl-p-[(10-phenyldecyl)amino]benzoate | 0.1 | 11 | 23 |
|  | 0.05 | 15 | 42 |
| Ethyl-p-[(5-phenylpentyl)amino]benzoate | 0.1 | 10 | 38 |
|  | 0.05 | 15 | 34 |
| p-[4-(2-Thienylbutyl)amino]benzoate | 0.1 | 23 | 10 |
| p-[(p-Fluorophenethyl)amino]benzoic acid | 0.1 | 11 | 46 |

TABLE I-continued

| Compound | % Compound in Diet | Lowering of Serum Sterol | Lowering of Serum Triglyceride |
|---|---|---|---|
| Ethyl-4-[(6-phenylhexyl)amino]-benzoate | 0.1 | 19 | 57 |
|  | 0.05 | 17 | 55 |
| Ethyl-4-[2-(2-thienyl)ethylamino]-benzoate | 0.1 | 15 | 31 |
| p-{[p-(Heptyloxy)benzyl]amino}-benzoic acid | 0.1 | 17 | 28 |
|  | 0.05 | 17 | 30 |
| Ethyl-p-{{3-[p-(benzyloxy)phenyl]-propyl}-amino}benzoate | 0.1 | 4 | 45 |

[1]The results 15 and 52 were obtained from a 4 week study.

The compounds of the present invention are useful as hypolipidemic agents in mammals when administered in amounts ranging from about 0.5 mg. per kg. to about 40 mg. per kg. of body weight per day. A preferred dosage regimen for optimum results would be from about 2 mg. per kg. to about 29 mg. per kg. of body weight per day. Thus the daily dosage employed for a subject of about 70 kg. is about 35 mg. to about 2.8 g. and preferably about 140 mg. to about 2.0 g.

The active compounds of the present invention may be orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum or the like. Such compositions and preparations should contain at least 0.1% of active compound. The percentage in the compositions and preparations may, of course, be varied and may conveniently be between about 5% and 75% or more of the weight of the unit. The amount of active compound in such therapeutically useful compositions or preparations is such that a suitable dosage will be obtained. Preferred compositions or preparations are prepared so that an oral dosage unit form contains between about 10 mg. and 500 mg. of active compound.

The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring. When the dosage unit form is a capsule, it may contain in addition to materials of the above type a liquid carrier such as a fatty oil. Various other materials may be present as coatings or to otherwise modify the physical form of the dosage unit. For instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Any material used in preparing any dosage unit form should be pharmaceutically pure and substantially non-toxic in the amounts employed. In addition, the active ingredients may be incorporated into sustained release preparations.

We claim:

1. A compound of the formula:

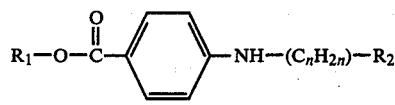

wherein n is an integer from 1 to 16; $R_1$ is selected from the group consisting of hydrogen and alkyl having from 1 to 6 carbon atoms; $R_2$ is selected from the group consisting of 4-halophenyl, 2,4-dihalophenyl, 2,4,6-trihalophenyl, 4-benzyloxyphenyl and 4-biphenyl; and the pharmaceutically acceptable acid-addition salts thereof and the alkali metal or organic base carboxylic acid salts thereof when $R_1$ is hydrogen.

2. The compound according to claim 1; 4-[(p-chlorobenzyl)amino]benzoic acid.

3. The compound according to claim 1; sodium 4-[(p-chlorobenzyl)amino]benzoate.

4. The compound according to claim 1; ethyl 4-[(p-chlorobenzyl)amino]benzoate.

5. The compound according to claim 1; 4-[(p-fluorophenethyl)amino]benzoic acid.

6. The compound according to claim 1; methyl 4-[(p-fluorophenethyl)amino]benzoate.

7. The compound according to claim 1; 4-[3-(p-chlorophenyl)propylamino]benzoic acid.

8. The compound according to claim 1; ethyl 4-[3-(p-chlorophenyl)propylamino]benzoate.

9. The compound according to claim 1; 4-[(4-biphenylmethyl)amino]benzoic acid.

10. The compound according to claim 1; ethyl 4-[(4-biphenylmethyl)amino]benzoate.

11. The compound according to claim 1; 4-[(p-benzyloxybenzyl)amino]benzoic acid.

12. The compound according to claim 1; ethyl 4-[(p-benzyloxybenzyl)amino]benzoate.

13. The compound according to claim 1; 4-[(p-benzyloxyphenethyl)amino]benzoic acid.

14. The compound according to claim 1; ethyl 4-[(p-benzyloxyphenethyl)amino]benzoate.

15. The compound according to claim 1; 4-{[3-(p-benzyloxyphenyl)propyl]amino}benzoic acid.

16. The compound according to claim 1; ethyl 4-{[3-(p-benzyloxyphenyl)propyl]amino}benzoate.

17. A compound according to claim 1, wherein $R_2$ is 4-halophenyl.

* * * * *